(12) United States Patent
Cohen (10) Patent No.: US 8,273,104 B2
(45) Date of Patent: Sep. 25, 2012

(54) ANTIMICROBIAL SUTURES AND METHODS OF MAKING THEM

(75) Inventor: Matthew Cohen, Berlin, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1043 days.

(21) Appl. No.: 11/485,591

(22) Filed: Jul. 11, 2006

(65) Prior Publication Data

US 2007/0010856 A1    Jan. 11, 2007

Related U.S. Application Data

(60) Provisional application No. 60/698,154, filed on Jul. 11, 2005.

(51) Int. Cl.
  *A61B 17/04* (2006.01)
  *A61L 33/00* (2006.01)
(52) U.S. Cl. .......................... 606/228; 427/2.1
(58) Field of Classification Search ............. 606/228, 606/231; 427/2.1, 2.24, 2.28
  See application file for complete search history.

(56) References Cited

U.S. PATENT DOCUMENTS

| | | | |
|---|---|---|---|
| 3,187,752 A | 6/1965 | Glick | |
| 3,565,077 A | 2/1971 | Glick | |
| 4,014,973 A | 3/1977 | Thompson | |
| 4,024,871 A * | 5/1977 | Stephenson | 606/231 |
| 4,043,344 A | 8/1977 | Landi et al. | |
| 4,047,533 A | 9/1977 | Perciaccante et al. | |
| 4,105,034 A | 8/1978 | Shalaby et al. | |
| 4,201,216 A | 5/1980 | Mattei | |
| 4,983,180 A * | 1/1991 | Kawai et al. | 606/230 |
| 5,019,093 A | 5/1991 | Kaplan et al. | |
| 5,059,213 A | 10/1991 | Chesterfield et al. | |
| 5,123,912 A | 6/1992 | Kaplan et al. | |
| 5,133,738 A | 7/1992 | Korthoff et al. | |
| 5,181,923 A | 1/1993 | Chesterfield et al. | |
| 5,226,912 A | 7/1993 | Kaplan et al. | |
| 5,261,886 A | 11/1993 | Chesterfield et al. | |
| 5,306,289 A | 4/1994 | Kaplan et al. | |
| 5,312,642 A | 5/1994 | Chesterfield et al. | |
| 5,318,575 A | 6/1994 | Chesterfield et al. | |
| 5,370,031 A | 12/1994 | Koyfman et al. | |
| 5,383,387 A | 1/1995 | Chesterfield et al. | |
| 5,447,100 A | 9/1995 | Chesterfield et al. | |
| 5,540,773 A | 7/1996 | Chesterfield et al. | |
| 5,662,682 A | 9/1997 | Chesterfield et al. | |
| 5,667,528 A | 9/1997 | Colligan | |
| 5,716,376 A | 2/1998 | Roby et al. | |
| 6,106,505 A * | 8/2000 | Modak et al. | 604/265 |
| 6,203,564 B1 | 3/2001 | Hutton et al. | |
| 6,277,927 B1 | 8/2001 | Roby et al. | |
| 6,494,898 B1 | 12/2002 | Roby et al. | |

(Continued)

FOREIGN PATENT DOCUMENTS

EP    0 499 048    8/1992

(Continued)

OTHER PUBLICATIONS

European Search Report (EP 06 01 2688 dated Aug. 1, 2007).

(Continued)

*Primary Examiner* — Corrine M McDermott
*Assistant Examiner* — Christina Lauer (57) ABSTRACT

Multifilament sutures are prepared by permeating the suture with an antimicrobial solution and applying an antimicrobial coating to the suture.

12 Claims, 3 Drawing Sheets

* FillandCoat-01 - produced from 0.5% triclosan in fill solution and 1.3% triclosan in coat solution.
* FillandCoat-02 - produced from 0.6% triclosan in fill solution and 1.0% triclosan in coat solution.
* FillandCoat-03 - produced from 1.3% triclosan in fill solution and 0.5% triclosan in coat solution.
  Total extractable triclosan per weight of suture for these samples is about 0.62% (as compared to the 0.02% in Vicryl Plus.)

U.S. PATENT DOCUMENTS

| | | |
|---|---|---|
| 6,566,419 B2 | 5/2003 | Denesuk |
| 6,596,657 B1 | 7/2003 | Shalaby |
| 2002/0077661 A1 | 6/2002 | Saadat |
| 2003/0149447 A1 | 8/2003 | Morency et al. |
| 2004/0010275 A1 | 1/2004 | Jacobs et al. |
| 2004/0068293 A1* | 4/2004 | Scalzo et al. .............. 606/228 |
| 2004/0068294 A1 | 4/2004 | Scalzo et al. |
| 2004/0147629 A1* | 7/2004 | Roby ........................ 523/105 |
| 2004/0185250 A1 | 9/2004 | John |

FOREIGN PATENT DOCUMENTS

| | | |
|---|---|---|
| EP | 0 647 452 | 10/2000 |
| WO | WO 98/00065 | 1/1998 |
| WO | WO 00/57933 | 10/2000 |
| WO | WO 2004/045663 | 6/2004 |
| WO | WO 2004/066927 | 8/2004 |
| WO | WO 2006/079469 A1 | 8/2006 |

OTHER PUBLICATIONS

European Search Report (EP 06 01 2688 dated Oct. 9, 2007).

European Search Report for EP 09014684.6-1219 date of completion is Apr. 22, 2010 (3 pages).

European Search Report for EP 10177651.6-1526 date of completion is Dec. 14, 2010 (3 pages).

* cited by examiner

FIG. 1

* FillandCoat-01 - produced from 0.5% triclosan in fill solution and 1.3% triclosan in coat solution.
* FillandCoat-02 - produced from 0.8% triclosan in fill solution and 1.0% triclosan in coat solution.
* FillandCoat-03 - produced from 1.3% triclosan in fill solution and 0.5% triclosan in coat solution.
Total extractable triclosan per weight of suture for these samples is about 0.62% (as compared to the 0.02% in Vicryl Plus.)

ANTIMICROBIAL SUTURES AND METHODS OF MAKING THEM

CROSS-REFERENCE TO RELATED APPLICATIONS

This application claims the benefit of U.S. Provisional Patent Application No. 60/698,154 filed Jul. 11, 2005, the entire disclosure of which is hereby incorporated by reference herein.

TECHNICAL FIELD

The present disclosure relates to antimicrobial multifilament sutures and to methods for preparing and using such sutures.

BACKGROUND OF RELATED ART

Absorbable multifilament sutures are known in the art. Such sutures include DEXON® sutures (made from a glycolide homopolymer and commercially available from Davis & Geck, Danbury, Conn.), VICRYL® sutures (made from a copolymer of glycolide and lactide and commercially available from Ethicon, Inc., Sommerville, N.J.), and POLYSORB® sutures (also made from a copolymer of glycolide and lactide and commercially available from United States Surgical Corporation, Norwalk, Conn.). These sutures are sometimes referred to as short term absorbable sutures, i.e., sutures which retain at least about 20 percent of their original strength at three weeks after implantation, with the suture mass being essentially absorbed in the body within about 60 to about 90 days post implantation.

Suture coatings for synthetic absorbable multifilament sutures are also known and are frequently utilized to improve physical characteristics of the sutures, including their knot tie-down properties. Known coatings include copolymers and homopolymers of glycolide, lactide, caprolactone, trimethylene carbonate, and dioxanone, as well as mixtures and blends thereof. For example, U.S. Pat. No. 5,123,912, the entire disclosure of which is incorporated by reference herein, discloses a bioabsorbable coating composition for surgical sutures which can be either a copolymer of a low molecular weight polyalkylene glycol, a glycolide monomer and a lactide monomer, or a copolymer of a low molecular weight polyalkylene glycol and a preformed copolymer of lactide and glycolide.

One problem with any surgical device, including sutures, is the potential for bacteria to adhere to the device and utilize the device as a means to enter the surrounding tissue in a patient. Known synthetic absorbable multifilament sutures do not yet provide effective levels of antimicrobial activity for the period of time the suture is in place. Therefore, contamination and infection can occur at the wound site prior to the complete healing of the wound closure.

Accordingly, there is a need for synthetic absorbable multifilament sutures that can remain in vivo for extended periods of time with enhanced antimicrobial efficacy. There is also a need for an easy and inexpensive method of applying an antimicrobial agent to a suture that provides protection against microorganisms for extended periods of time.

SUMMARY

Methods for producing antimicrobial sutures are provided wherein multifilament sutures can be permeated with an antimicrobial solution and coated with a separate antimicrobial coating. The antimicrobial solution can be applied before, or after, the antimicrobial coating.

In embodiments, the method may include providing a multifilament suture, permeating the multifilament suture with an antimicrobial solution, and applying an antimicrobial coating onto at least a portion of the surface of the permeated multifilament suture.

In other embodiments, the method may include providing a multifilament suture, applying an antimicrobial coating onto at least a portion of the surface of the multifilament suture, cracking the coated multifilament suture, and permeating the cracked coated multifilament suture with an antimicrobial solution.

Sutures with these coatings, as well as methods for closing wounds with these sutures, are also provided.

In embodiments, a suture of the present disclosure may include a plurality of filaments with interstitial spaces defined by the plurality of filaments, an antimicrobial agent filling at least a portion of the interstitial spaces, and an antimicrobial coating on at least a portion of the plurality of filaments. In other embodiments, a suture of the present disclosure may include a plurality of filaments with interstitial spaces defined by the plurality of filaments, an antimicrobial solution including triclosan and methylene chloride permeating at least a portion of the interstitial spaces, and an antimicrobial coating including triclosan, a glycolide/caprolactone copolymer, and calcium stearoyl lactylate covering at least a portion of the plurality of filaments.

Still other sutures encompassed by the present disclosure include braided sutures having antimicrobial properties formed from a plurality of polymeric filaments, said filaments being formed from a polymeric material that is absorbable under physiological conditions, and a coating material disposed on said elongate braided structure, said coating including a film-forming polymer, a salt of a fatty acid ester, and an antimicrobial agent selected from the group consisting of antibiotics, antiseptics, disinfectants and combinations thereof.

A method of closing a wound in accordance with the present disclosure may include providing a suture having a plurality of filaments with interstitial spaces defined by the plurality of filaments, an antimicrobial solution within said interstitial spaces, and an antimicrobial coating on at least a portion of the plurality of filaments, attaching said suture to a needle to produce a needled suture, and passing said needled suture through tissue to create wound closure.

In embodiments, the present disclosure also provides an antimicrobial composition including an antiseptic, a film-forming polymer, and a salt of a fatty acid ester such as magnesium stearoyl lactylate, aluminum stearoyl lactylate, barium stearoyl lactylate, zinc stearoyl lactylate calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, zinc olelyl lactylate and calcium stearoyl lactylate.

In other embodiments, a suitable antimicrobial composition may include triclosan, a glycolide/caprolactone copolymer, and calcium stearoyl lactylate.

DETAILED DESCRIPTION

The sutures of the present disclosure may be prepared at least in part from a plurality of filaments. An antimicrobial solution which contains at least one antimicrobial agent and at least one solvent may be applied to the suture. An antimicrobial coating containing at least one antimicrobial agent, at least one film-forming polymer, and at least one fatty acid ester may also be applied to the suture. The antimicrobial coating may be applied either before or after the antimicrobial solution is applied to the multifilament suture.

The filaments from which the suture may be made can be any synthetic absorbable fiber-forming material. Thus, for example, the filaments can be made from synthetic absorbable polymers such as those made from glycolide, lactide, caprolactone, alkylene carbonates (i.e. trimethylene carbonate), dioxanones, and copolymers and combinations thereof. In embodiments, a suture may be constructed of a combination including glycolide and lactide, in some embodiments a copolymer thereof.

The suture can be made from the filaments using any known technique such as, for example, braiding, weaving or knitting. The filaments may also be combined to produce a non-woven suture. The filaments themselves may be drawn, oriented, crinkled, twisted, commingled or air entangled to form yarns as part of the suture forming process. The suture should possess interstices or spaces between the filaments (or overlapping areas of the same filament) into which the antimicrobial solution with which the suture is permeated can flow.

In one embodiment the multifilament suture of the present disclosure can be produced by braiding. The braiding can be done by any method within the purview of those skilled in the art. For example, braid constructions for sutures and other medical devices are described in U.S. Pat. Nos. 5,019,093, 5,059,213, 5,133,738, 5,181,923, 5,226,912, 5,261,886, 5,306,289, 5,318,575, 5,370,031, 5,383,387, 5,662,682, 5,667,528, and 6,203,564, the entire disclosures of each of which are incorporated by reference herein. Once the suture is constructed, it can be sterilized by any means within the purview of those skilled in the art.

In some cases a tubular braid, or sheath, may be constructed about a core structure which is fed through the center of the braider. Known tubular braided sutures, including those possessing cores, are disclosed, for example, in U.S. Pat. Nos. 3,187,752, 3,565,077, 4,014,973, 4,043,344, and 4,047,533.

In one embodiment, a multifilament suture is first contacted with an antimicrobial solution, and an antimicrobial coating is then applied to the suture. The antimicrobial solution contains at least one antimicrobial agent and at least one solvent, which carries the antimicrobial agent to the interstices or spaces between the filaments and, where present, to the core of the suture. The term "antimicrobial agent" as used herein includes antibiotics, antiseptics, disinfectants and combinations thereof that are soluble in organic solvents such as alcohols, ketones, ethers, aldehydes, acetonitrile, acetic acid, methylene chloride, chloroform and water.

Classes of antibiotics that can be used in the antimicrobial solution include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam.

Examples of antiseptics and disinfectants which may be utilized in the antimicrobial solution include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

The antimicrobial solution can include any solvent or combination of solvents suitable for the chosen antimicrobial agent. To be suitable, the solvent must (1) be miscible with the antimicrobial agent, (2) not appreciably affect the integrity of any polymeric material used to form the suture filaments, and (3) be capable, in combination with the antimicrobial agent, of permeating into the interstices of the suture. Some examples of suitable solvents include alcohols, ketones, ethers, aldehydes, acetonitrile, acetic acid, methylene chloride, chloroform and water. In embodiments, methylene chloride may be used as a solvent.

Preparing the antimicrobial solution of the present disclosure is a relatively simple procedure and can be accomplished by blending, mixing, and the like. In one embodiment, where triclosan and methylene chloride are utilized to form the antimicrobial solution, the desired amount of triclosan is placed into a container, followed by the addition of the desired amount of methylene chloride. The two ingredients may then be mixed thoroughly to combine the ingredients.

The antimicrobial solution generally contains from about 0.001% to about 25% of the antimicrobial agent by weight. The exact amount of the antimicrobial agent will depend on a number of factors, such as the particular agent used, the suture being contacted, and the choice of solvent employed. In embodiments, for example, where the antimicrobial agent is an antiseptic, the antimicrobial solution may contain from about 0.01% to about 15% of the chosen antimicrobial agent. In other embodiments, the antimicrobial solution may contain from about 0.1% to about 10% of the antimicrobial agent.

Any known technique may be employed for applying the antimicrobial solution to the suture. Suitable techniques include dipping, spraying, wiping and brushing. In embodiments, the antimicrobial solution may be applied to the suture in its final form. Since the antimicrobial solution contains a solvent, a curing step may be employed to remove excess solvent, leaving the antimicrobial agent on the core, if present, and in the interstitial spaces of the braid, i.e., between the plurality of filaments utilized to form the multifilament suture. In embodiments, the antimicrobial agent alone remains in the interstitial spaces. In other embodiments some of the solvent also remains with the antimicrobial agent in the interstitial spaces, i.e., the antimicrobial solution remains in the interstitial spaces.

The amount of the antimicrobial solution applied should be an effective amount to provide antimicrobial properties to the suture. The exact amount will depend upon the configuration of the suture and the formulation of the solution. In embodiments, the antimicrobial solution may be applied in an amount from about 0.001 to about 25 weight percent (excluding any solvent) by weight of the suture. In one embodiment, the antimicrobial solution may be applied in an amount from about 0.01 to about 15 weight percent (excluding any solvent) by weight of the suture.

After removal of the solvent, an antimicrobial coating containing at least one antimicrobial agent and at least one film-forming polymer may be applied to the suture.

Film-forming polymers which may be utilized in the antimicrobial coating are within the purview of those skilled in the art and include glycolide, lactide, caprolactone, trimethylene carbonate, dioxanones, dioxepanones, etc., and copolymers and combinations thereof.

In embodiments, the film-forming polymer may include a caprolactone containing copolymer as described in U.S. Pat. No. 5,716,376, the entire disclosure of which is incorporated by reference herein. Such a caprolactone containing copolymer can be obtained by polymerizing a major amount of epsilon-caprolactone and a minor amount of at least one other copolymerizable monomer or mixture of such monomers in the presence of a polyhydric alcohol initiator.

Monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including alpha hydroxy acids (such as glycolic acid and lactic acid) and beta hydroxyacids (such as beta hydroxybutyric acid and gamma hydroxyvaleric acid); polyalkyl ethers (such as polyethylene glycol) and combinations thereof. In an embodiment, glycolide can be utilized as the comonomer with epsilon-caprolactone in the film-forming polymer.

Suitable polyhydric alcohol initiators which may be utilized in preparing the film-forming polymer include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being utilized in some embodiments.

The polyhydric alcohol initiator can be generally employed in small amounts, e.g., from about 0.01 to about 5 weight percent of the total monomer mixture, and in embodiments from about 0.1 to about 3 weight percent of the total monomer mixture.

The film-forming copolymer can contain from about 70 to about 98 weight percent epsilon-caprolactone derived units, in embodiments from about 80 to about 95 weight percent epsilon-caprolactone derived units, the balance of the copolymer being derived from the other copolymerizable monomer (s), such as glycolide.

In some embodiments, the coating compositions of the present disclosure may also include a fatty acid component that contains a fatty acid or a fatty acid salt or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to about 22 carbon atoms, and mixtures thereof. Fatty acid salts including the calcium, magnesium, barium, aluminum, and zinc salts of stearic, palmitic and oleic acids may be useful in some embodiments of the present disclosure. Some useful salts include commercial "food grade" calcium stearate which contains a mixture of about one-third $C_{16}$ and two-thirds $C_{18}$ fatty acids, with small amounts of the $C_{14}$ and $C_{22}$ fatty acids.

In embodiments, the antimicrobial coating includes a film-forming polymer combined with a salt of a fatty acid ester. Suitable salts of fatty acid esters include those of the formula:

wherein x is an alkaline-earth metal or ion thereof, and $R_1$ is $C_{10}$ or greater alkyl, $R_2$ is H or $C_1$-$C_3$ alkyl, $R_3$ is H or $C_1$-$C_3$ alkyl, $R_4$ is H or $C_1$-$C_3$ alkyl, $R_5$ is H or $C_1$-$C_3$ alkyl, and n>1. Such suitable fatty acids include calcium stearoyl-2-lactylate (such as the calcium stearoyl-2-lactylate commercially available under the tradename VERV from American Ingredients Co., Kansas City, Mo.). Other fatty acid ester salts which may be utilized include lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, francium olelyl lactylate, and combinations thereof.

Where utilized, the amount of fatty acid component can be from about 5 percent to about 50 percent by weight of the total coating composition. In embodiments, the fatty acid component may be present in an amount from about 10 percent to about 20 percent by weight of the total coating composition.

In one embodiment, the film-forming polymer, such as the caprolactone/glycolide copolymer described above, can be from about 45 to about 60 weight percent of the antimicrobial coating and the salt of a fatty acid ester can be from about 40 to about 55 weight percent of the antimicrobial coating. In embodiments, the film-forming polymer, such as the caprolactone/glycolide copolymer described above, can be from about 50 to about 55 weight percent of the antimicrobial coating and the salt of a fatty acid ester can be from about 45 to about 50 weight percent of the antimicrobial coating.

An antimicrobial agent may then be added to the film-forming polymer and salt of a fatty acid ester to produce an antimicrobial coating. As stated previously, the term "antimicrobial agent" as used in the present disclosure includes antibiotics, antiseptics, disinfectants and combinations thereof. In embodiments, the antimicrobial agent may be an antiseptic, such as triclosan. The antimicrobial agent used in the antimicrobial coating does not necessarily have to be the same antimicrobial agent used in the antimicrobial solution.

In one embodiment, a 52/48 weight percent mixture of glycolide/caprolactone polymer and calcium stearoyl lactylate can be combined with an antiseptic such as triclosan to create an antimicrobial coating.

The antimicrobial coating may contain from about 0.001% to about 25% of the antimicrobial agent by weight. The exact amount of the antimicrobial agent in the antimicrobial coating will depend upon a number of factors, such as the particular agent used, the composition of the suture being contacted, and the choice of coating material. In embodiments, for example where the antimicrobial agent is an antiseptic, the antimicrobial coating may contain from about 0.01% to about 15% of the chosen antimicrobial agent by weight. In other embodiments, the coating may contain from about 0.1% to about 10% of the chosen antimicrobial agent by weight.

In embodiments, the antimicrobial coating may be added to a solvent and applied to at least a portion of the surface of the suture. Any solvent suitable for use with the other materials of the antimicrobial coating may be utilized including, in embodiments, the solvents described above for use in forming the antimicrobial solution. The resulting coating solution may then be utilized to apply an antimicrobial coating to a suture.

The antimicrobial coating herein can be applied to a suture by any suitable process, e.g., by passing the suture through a solution of the copolymer, e.g., in toluene, methylene chloride, etc., past a brush or other coating solution applicator, or past one or more spray nozzles dispensing the suture coating solution. The suture wetted with the coating solution may be subsequently passed through or held in a drying oven for a time and at a temperature sufficient to vaporize and drive off the solvent.

If desired, the suture coating composition can optionally contain additional components, e.g., dyes, antibiotics, additional antiseptics, growth factors, anti-inflammatory agents, and the like.

While the coating composition herein could be applied to any type of suture, in embodiments it may be applied to a braided multifilament suture. The amount of coating composition applied to a braided suture will vary depending upon the structure of the suture, e.g., the number of filaments, tightness of braid or twist, the size of the suture, and its composition. The amount of antimicrobial coating applied should be an effective amount to provide antimicrobial properties to the suture. The exact amount to be applied to the suture, e.g. by coating, dipping, spraying, wiping or other appropriate techniques, will vary depending upon the coating material selected, the antimicrobial agent selected, and the specific construction of the suture being contacted. The antimicrobial coating may be applied in an amount from about 0.001 to about 25 percent by weight of the suture, in embodiments from about 0.01 to about 15 percent by weight of the suture.

Preparing the antimicrobial coating of the present disclosure may also be a relatively simple procedure. For example, in the case of a coating material containing glycolide/caprolactone copolymer, calcium stearoyl lactylate and triclosan, the desired amount of each of the necessary ingredients may be placed into a container and mixed thoroughly to combine the ingredients.

Both the antimicrobial solution and the antimicrobial coating may contain various optional ingredients, such as stabilizing agents, thickeners, colors, etc. The optional ingredients may represent up to about 10% of the total weight of either the antimicrobial solution or the antimicrobial coating.

It is also within the scope of the present disclosure to permeate and coat the multifilament suture with a pharmaceutically beneficial agent. A pharmaceutically beneficial agent includes a chemical or drug that, when introduced into tissue, exhibits a desired therapeutic effect upon said tissue. Examples of pharmaceutically beneficial agents include drugs like anti-inflammatories, steroids, growth factors, blood thinners, clotting factors, anti-hypertensives, immunosuppressants, anesthetics, etc.

As the application of the antimicrobial solution penetrates the interstices of the multifilament and, in embodiments, reaches the core of the suture, the process of applying the antimicrobial solution may be referred to as a fill process, and the application of the antimicrobial coating may be referred to as a coat process. In one embodiment, the sutures of the present disclosure may be prepared by an in-line fill and coat method. For the fill portion of the process, a multifilament suture may be passed through an applicator that applies an antimicrobial solution. In one embodiment the antimicrobial solution can include 1.3% by weight triclosan in methylene chloride. The methylene chloride can be flashed off the suture leaving triclosan on the suture core and in the interstices of the braided suture. The suture can then pass to a coating applicator where the antimicrobial coating is applied. In an embodiment, the antimicrobial coating can be a suspension formed by mixing a glycolide and caprolactone copolymer with calcium stearoyl lactate at a ratio of approximately 52/48, adding methylene chloride, ethanol, and hexanes while mixing, and then adding triclosan in an amount of from about 1% to about 0.5% of the total composition.

The antimicrobial coating of the present disclosure may also be used as an antimicrobial composition for other medicinal applications, including wound dressings, to promote wound healing.

In an alternate embodiment of the present disclosure, a multifilament suture may be first coated with a substance through which the antimicrobial solution cannot pass, e.g., the antimicrobial coating, followed by application of the antimicrobial solution. In such a case the suture should be treated to crack such coating prior to contact with the antimicrobial solution. This will allow the antimicrobial solution to flow into the interstices of the suture. Any technique within the purview of one skilled in the art may be used to crack the coating, such as, for example, calendering. Methods and apparatus for calendering sutures which may be utilized are disclosed in U.S. Pat. Nos. 5,540,773, 5,312,642 and 5,447,100, the entire disclosures of each of which are incorporated by reference herein. Once a suture coated with an antimicrobial coating has been calendered, the antimicrobial solution described above may be applied so that the antibacterial agent permeates into the interstices of the braid thereby remaining in the spaces between the filaments and on the core of the multifilament suture.

The resulting sutures of the present disclosure posses a plurality of filaments with interstitial spaces defined by the plurality of filaments. In some embodiments, the sutures of the present disclosure also include a core around which the plurality of filaments may be braided or twisted. As noted above, the antimicrobial solution of the present disclosure fills at least a portion of the suture by filling the interstices and remaining on the core, where present. The sutures of the present disclosure also posses an antimicrobial coating as described above on at least a portion of the plurality of filaments.

A suture prepared in accordance with the present disclosure may be attached to any surgical needle within the purview of those skilled in the art to produce a needled suture. Wounds may be sutured by passing a needled suture through tissue to create wound closure. The needle may then be removed from the suture and the suture tied. The suture may remain in the tissue and help prevent contamination and infection of said tissue by virtue of its antimicrobial properties, thereby promoting wound healing and minimizing infection. The suture coating also advantageously enhances the surgeon's ability to pass the suture through tissue, and increases the ease and security with which he/she can tie the suture.

The following examples are given as an illustration of the preparation and superior characteristics of the sutures described herein. It should be noted that the present disclosure is not limited to the specific details embodied in the examples.

EXAMPLE 1

Sutures were prepared with antimicrobial solutions and antimicrobial coatings of the present disclosure. POLYSORB® 2/0 sutures were first filled with antimicrobial solutions (the "fill") having varying amounts of triclosan in methylene chloride. The methylene chloride was flashed off leaving the triclosan in the interstices of the filaments and on the core, and the antimicrobial coating (the "coat") was then applied. The antimicrobial coating was a 52/48 mixture of a glycolide/caprolactone copolymer and calcium stearoyl lactylate with varying amounts of triclosan. Details of the fill and coat are set forth in Table 1 below.

TABLE 1

CHEMICAL ANALYSIS OF FILL-AND-COATS
TOTAL TRICLOSAN CONTENT

| Sample ID | Suture Treatment (% triclosan in fill and coat) | % triclosan (per wt. suture) | ppm triclosan | ug/m triclosan |
|---|---|---|---|---|
| 1 | Fill 0.5%, Coat 1.3% | 0.60 | 5964 | 805 |
| 2 | Fill 0.8%, Coat 1.0% | 0.64 | 6367 | 860 |
| 3 | Fill 1.3%, Coat 0.5.% | 0.64 | 6403 | 860 |
| 4 | Core extracted only | 0.06 | 595 | |
| 5 | Core extracted only | 0.07 | 671 | |
| VICRYL ® Plus | less than 50 ug/m | 0.02 | 225 | 20 |

The sutures were then suspended in nutrient broth injected with a $10^3$ inoculum of *Staphylococcus epidermidis*. Test sutures and a control suture (untreated POLYSORB® suture) were sampled (n=3) after 24, 48, 72, 96, 120, 144 and 168 hours. The ability of the sutures to inhibit formation of colonies of *Staphylococcus epidermidis* were also compared with VICRYL® and VICRYL® Plus sutures, both commercially available from Ethicon, Inc., (Somerville, N.J.). (VICRYL® sutures are made of a co-polymer of 90% glycolide and 10% lactide; VICRYL® Plus sutures are the VICRYL® suture with a triclosan coating). As noted above in Table 1, the total extractable triclosan per weight of the sutures of the present disclosure was about 0.62%, compared with only 0.02% for the VICRYL® Plus sutures.

Figure 1:
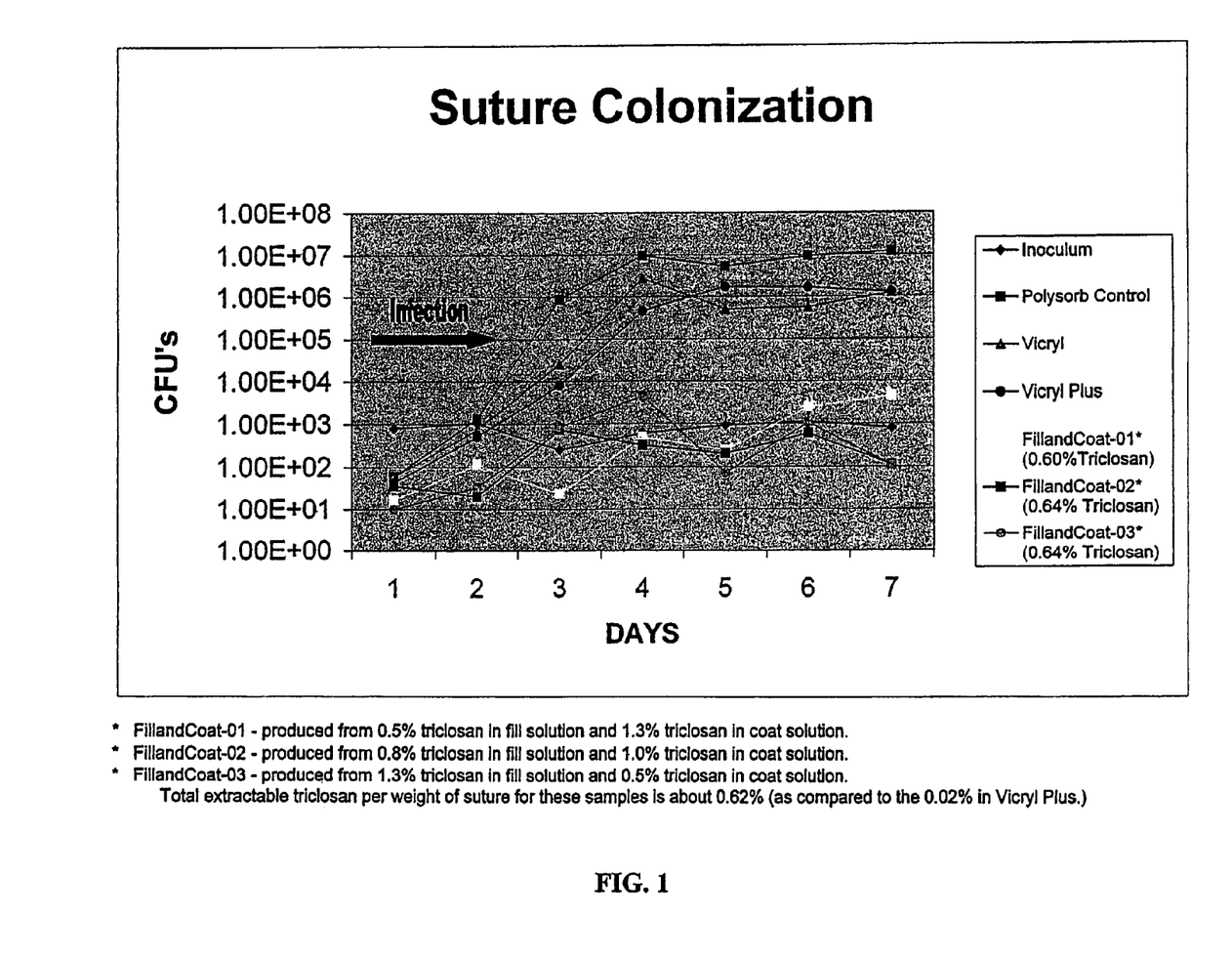
FIG. 1 is a graph depicting colonization of sutures of the present disclosure with varying concentrations of antimicrobial agents by *Staphylococcus epidermidis*.

At each 24 hour interval, sutures not removed from the test for analysis were re-inoculated with a fresh $10^3$ inoculum. For each test suture, any biofilm that formed on its surface was removed, incubated on nutrient agar, and quantified in units of CFUs (colony forming units). The CFUs were plotted per unit time for each test suture. The results of these tests are set forth in FIG. 1. Test sutures that contained CFUs in an amount at least 2 logs less than the control were considered to have anti-biofilm properties. The amount of time that the test suture maintained CFU counts at least 2 logs less than the control was representative of the duration of the anti-biofilm efficacy of the test suture. As can be seen in FIG. 1, the sutures treated in accordance with the present disclosure had lower levels of CFUs compared with the untreated POLYSORB®E control suture, the VICRYL® suture, and the VICRYL® Plus suture.

Figure 2A:
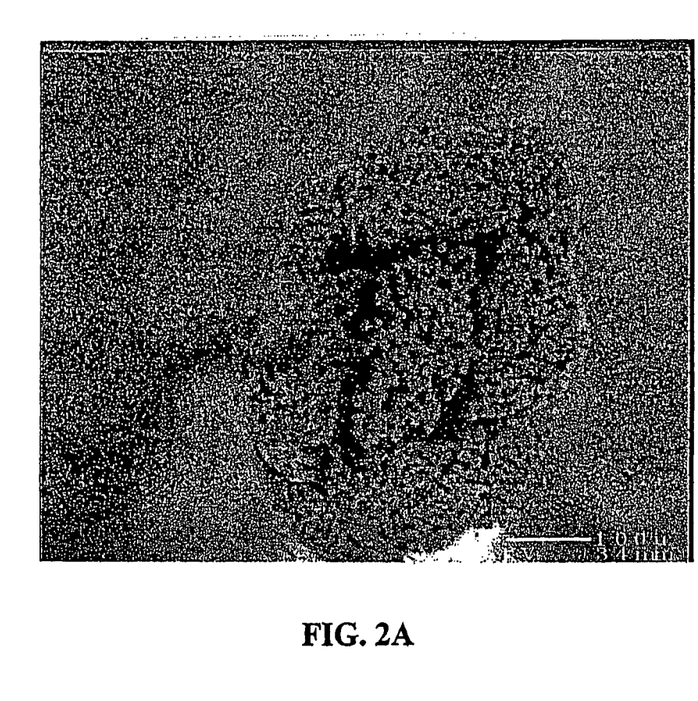
FIGS. 2A and 2B are scanning electron microscope ("SEM") images of a POLYSORB® 2/0 suture treated in accordance with the present disclosure and a VICRYL® Plus 2/0 suture, respectively.
Figure 2B:
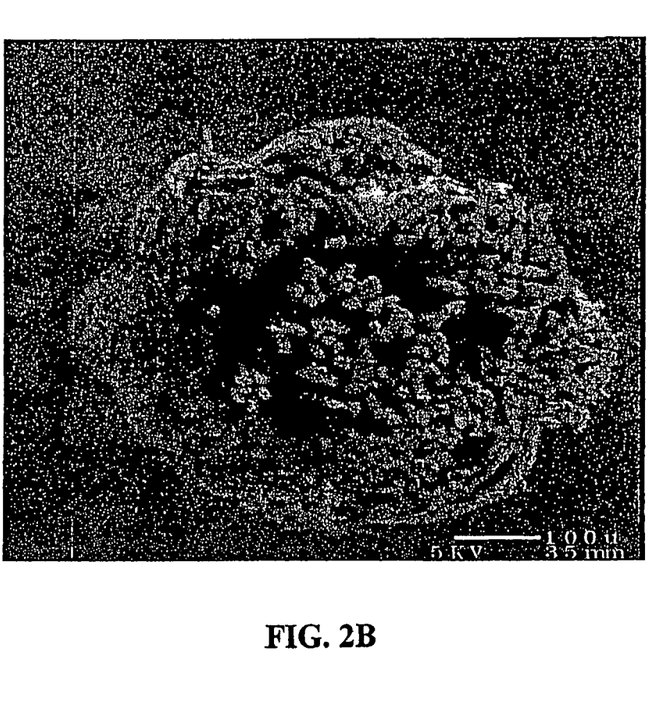

Scanning electron microscope ("SEM") images of sutures of the present disclosure were also obtained and compared with SEM images of VICRYL® Plus sutures; the SEM images are set forth as FIGS. 2A and 2B, respectively. As can be seen in comparing FIG. 2A (a POLYSORB® 2/0 suture with a fill and coat of the present disclosure) with FIG. 2B (a VICRYL® Plus 2/0 suture), triclosan applied with the fill and coat method of the present disclosure penetrated through the sheath fibers into the core; this penetration was not present in the VICRYL® Plus sutures.

EXAMPLE 2

Figure 3:
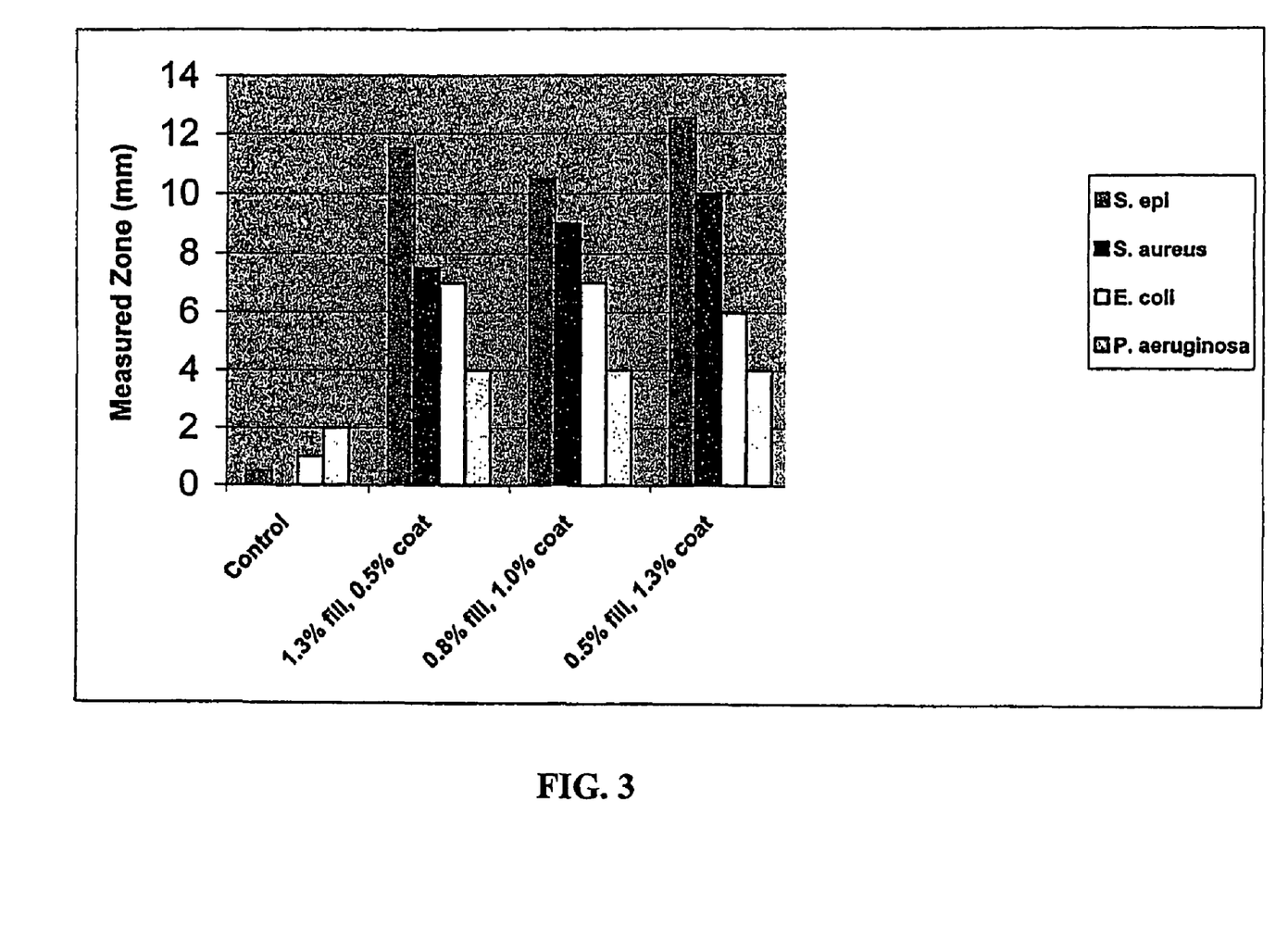
FIG. 3 is a graph depicting zone of inhibition results for sutures of the present disclosure when exposed to *Staphylococcus epidermidis, Staphylococcus aureus, Escherichia coli* and *Pseudomonas aeruginosa*.

Sutures prepared in Example 1 were subjected to zone of inhibition testing by contacting them with *Staphylococcus epidermidis, Staphylococcus aureus, Escherichia coli* and *Pseudomonas aeruginosa*. The results of these tests are set forth in FIG. 3. As can be seen in FIG. 3, the sutures of the present disclosure had enhanced antibacterial activity compared with the untreated POLYSORB® suture. Cytotoxicity testing of the sutures was also conducted, with the sutures of the present disclosure eliciting no toxic response.

It will be understood that various modifications may be made to the embodiments disclosed herein. Therefore, the above description should not be construed as limiting, but merely as exemplifications of preferred embodiments. Those skilled in the art will envision other modifications within the scope and spirit of this disclosure.

What is claimed is:

1. A method comprising:
   providing a multifilament suture;
   permeating the multifilament suture with an antimicrobial solution; and
   applying an antimicrobial coating containing about 5% to about 25% of an antimicrobial agent and from about 10 percent to about 20 percent of one or more fatty acid components onto at least a portion of the surface of the permeated multifilament suture.

2. The method of claim 1 wherein the antimicrobial solution comprises at least one antimicrobial agent selected from the group consisting of antibiotics, antiseptics, disinfectants and combinations thereof.

3. The method of claim 1 wherein the antimicrobial solution comprises triclosan.

4. The method of claim 1 wherein the antimicrobial solution comprises at least one solvent selected from the group consisting of alcohols, ketones, ethers, aldehydes, acetonitrile, acetic acid, methylene chloride, chloroform and water.

5. The method of claim 1 wherein the antimicrobial coating comprises at least one antimicrobial agent and at least one film-forming polymer.

6. The method of claim 1 wherein the antimicrobial coating comprises at least one antimicrobial agent selected from the group consisting of antibiotics, antiseptics, disinfectants and combinations thereof.

7. The method of claim 1 wherein the antimicrobial coating comprises triclosan.

8. The method of claim 1 wherein the antimicrobial coating comprises at least one film-forming polymer that contains linkages derived from one or more monomers selected from the group consisting of glycolide, lactide, caprolactone, trimethylene carbonate, dioxanones and dioxepanones.

9. The method of claim 1 wherein the antimicrobial coating comprises a glycolide/caprolactone copolymer as the film-forming polymer.

10. The method of claim 1 wherein the one or more fatty acid components are selected from the group consisting of fatty acids, fatty acid salts and fatty acid esters.

11. The method of claim 1 wherein the one or more fatty acid components comprises at least one salt of a fatty acid ester selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, zinc palmityl lactylate, calcium olelyl lactylate, magnesium olelyl lactylate, aluminum olelyl lactylate, barium olelyl lactylate, zinc olelyl lactylate, and calcium stearoyl lactylate.

12. The method of claim 1 wherein the one or more fatty acid components is calcium stearoyl lactylate.

* * * * *